United States Patent
Wang et al.

(10) Patent No.: US 9,706,967 B2
(45) Date of Patent: Jul. 18, 2017

(54) ENERGY-WEIGHTED SINGLE-BINNING FOR A PHOTON-COUNTING DETECTOR

(71) Applicant: TOSHIBA MEDICAL SYSTEMS CORPORATION, Otawara-Shi (JP)

(72) Inventors: Gin-Chung Wang, Lincolnshire, IL (US); Daniel Gagnon, Twinsburg, OH (US); Yu Zou, Naperville, IL (US)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 203 days.

(21) Appl. No.: 14/212,637

(22) Filed: Mar. 14, 2014

(65) Prior Publication Data
US 2015/0257722 A1 Sep. 17, 2015

(51) Int. Cl.
*A61B 6/03* (2006.01)
*A61B 6/00* (2006.01)
*G01N 23/087* (2006.01)
*G01T 1/29* (2006.01)

(52) U.S. Cl.
CPC ............ *A61B 6/4241* (2013.01); *A61B 6/032* (2013.01); *G01N 23/087* (2013.01); *G01T 1/2985* (2013.01)

(58) Field of Classification Search
CPC .... A61B 6/4241; A61B 6/482; G01N 23/087; G01N 2223/50; G01T 1/36
See application file for complete search history.

(56) References Cited

U.S. PATENT DOCUMENTS

2004/0264628 A1* 12/2004 Besson ............... A61B 6/508
378/5
2007/0076842 A1* 4/2007 Tkaczyk ............. A61B 6/032
378/5

FOREIGN PATENT DOCUMENTS

JP 2006-101926 A 4/2006

OTHER PUBLICATIONS

Taly Gilat Schmidt, et al, "Optimal "image-based" weighting for energy-resolved CT" Medical Physics, vol. 36, No. 7, Jul. 2009, pp. 3018-3027 (reference previously filed, submitting additional pages).

\* cited by examiner

*Primary Examiner* — Thomas R Artman
(74) *Attorney, Agent, or Firm* — Oblon, McClelland, Maier & Neustadt, L.L.P.

(57) ABSTRACT

An apparatus is provided that includes a digital processing circuit to obtain a digital signal corresponding to an output signal of a photon-counting detector; determine, from the obtained digital signal, a plurality of X-ray photons received by the photon-counting detector during a measurement period; determine a corresponding energy level of each of the plurality of X-ray photons; determine, based on the corresponding energy level, a corresponding weight for each of the plurality of X-ray photons; and calculate a sum of the corresponding weights of the plurality of X-ray photons.

12 Claims, 6 Drawing Sheets

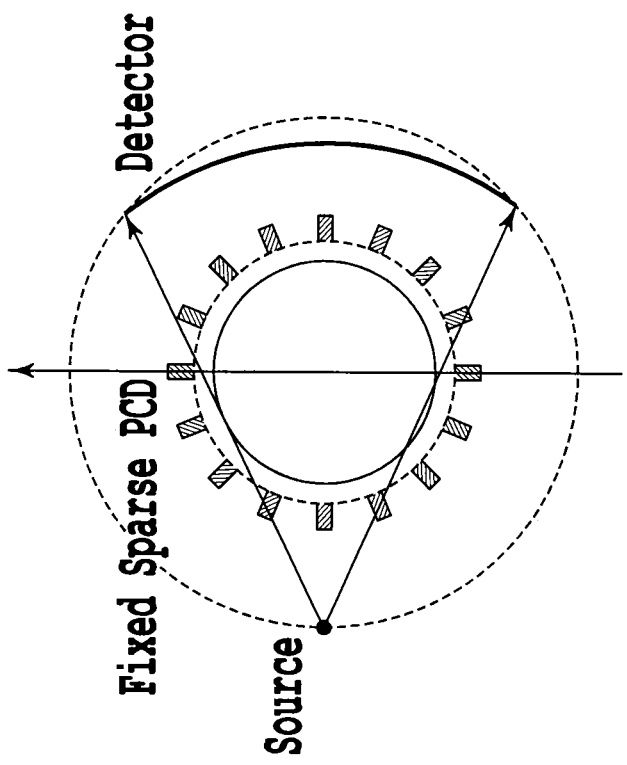
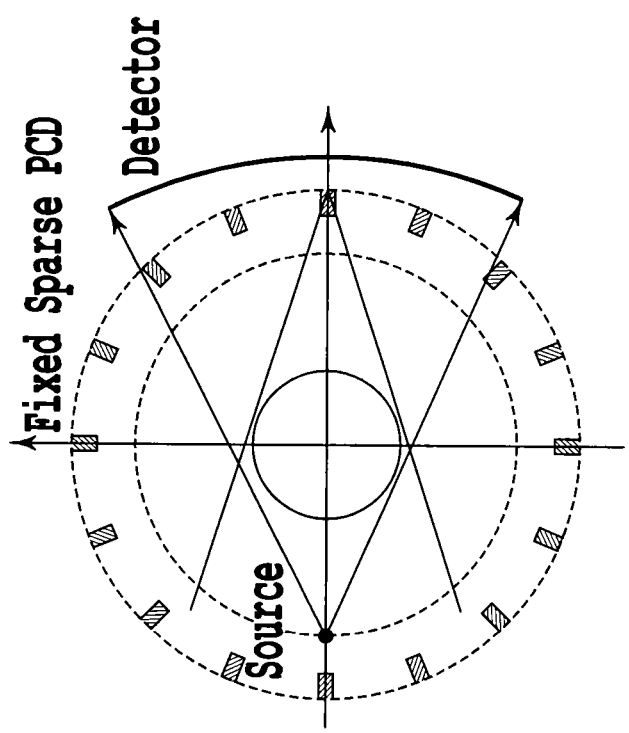
*Fig. 6B*
*Fig. 6A*

ENERGY-WEIGHTED SINGLE-BINNING FOR A PHOTON-COUNTING DETECTOR

FIELD

Embodiments disclosed herein generally relate to photon-counting detectors and computed tomography (CT) imaging using photon-counting detectors.

BACKGROUND

In conventional spectral CT imaging, it has been shown that energy-weighting, whether in the image-domain or the data-domain, improves the contrast-to-noise ratio. Conventionally, photon-counting detectors use a set of predetermined energy thresholds to count the number of events falling into predetermined energy ranges. However, no practical implementation of energy-weighting at the detector level is known.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIGS. 6A and 6B illustrate fourth-generation scanners having photon-counting detectors.

DETAILED DESCRIPTION

According to one embodiment, there is provided an apparatus, comprising a digital processing circuit configured to (1) obtain a digital signal corresponding to an output signal of a photon-counting detector; (2) determine, from the obtained digital signal, a plurality of X-ray photons received by the photon-counting detector during a measurement period; (3) determine a corresponding energy level of each of the plurality of X-ray photons; (4) determine, based on the corresponding energy level, a corresponding weight for each of the plurality of X-ray photons; and (5) calculate a sum of the corresponding weights of the plurality of X-ray photons.

In another embodiment, the apparatus includes an analog-to-digital converter circuit configured to generate the digital signal from the output signal of the photon-counting detector.

In another embodiment, the apparatus includes a preamplifier configured to amplify the output signal of the photon-counting detector to generate an amplified signal, wherein the amplified signal is input to the analog-to-digital converter circuit.

In another embodiment, the digital processing circuit is configured to determine the corresponding weight to be proportional to an inverse of the corresponding energy level cubed.

In another embodiment, the digital processing circuit is configured to determine the corresponding weight by accessing a programmable look-up table.

In another embodiment, the apparatus includes a memory configured to store the calculated sum as an energy-weighted bin value.

According to another embodiment, there is provided a computed tomography scanner, comprising: (1) an X-ray source; (2) a plurality of photon-counting detectors; and (3) a plurality of data acquisition devices, each data acquisition device including a digital processing circuit configured to obtain a digital signal corresponding to an output signal of a photon-counting detector; determine, from the obtained digital signal, a plurality of X-ray photons received by the photon-counting detector during a measurement period; determine a corresponding energy level of each of the plurality of X-ray photons; determine, based on the corresponding energy level, a corresponding weight for each of the plurality of X-ray photons; and calculate a sum of the corresponding weights of the plurality of X-ray photons.

Figure 1:
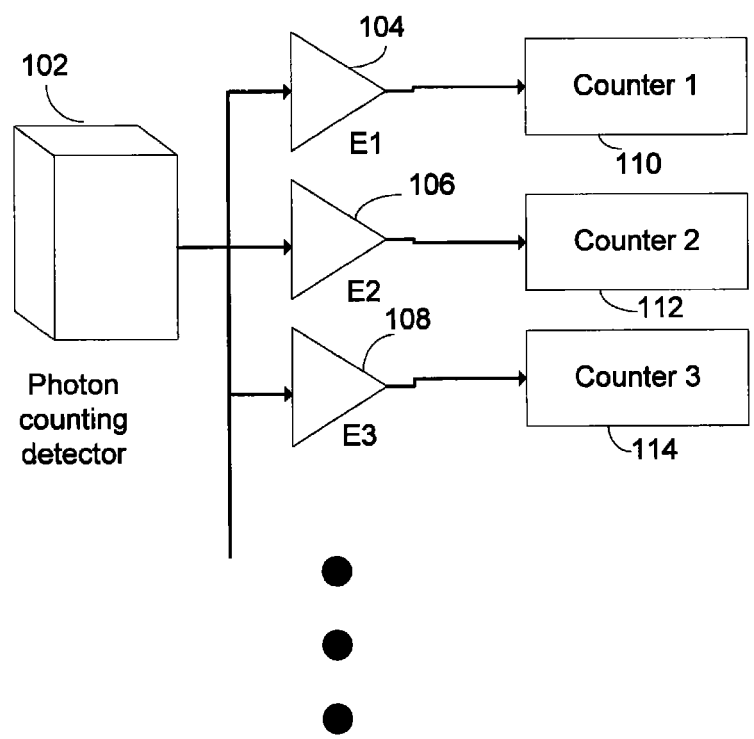
FIG. 1 is a block diagram of a photon-counting detector connected to a set of comparators with predetermined energy thresholds to count the number of events falling in predetermined energy ranges.

Referring now to the drawings, wherein like reference numerals designate identical or corresponding parts throughout the several views, FIG. 1 illustrates a system in which the signal output from a photon-counting detector device 102 is input into a set of comparators 104, 106, and 108, etc. The comparators 104, 106, and 108 have a corresponding set of predetermined energy thresholds, denoted by E1, E2, and E3, etc. and one of the comparators produces an output signal when the energy level of the signal output from the photon-counting detector falls within a corresponding one of the energy ranges determined by the predetermined energy thresholds. The output of each comparator is connected to a corresponding counter 110, 112, and 114, etc., which counts the number of received photons at the corresponding energy range.

However, the approach illustrated in FIG. 1 is limited because the finite number of energy thresholds (E1, E2, E3 . . . ) defeats the possibility of energy-weighted binning at the detector level.

Thus, according to one embodiment, a device that performs energy-weighted binning at the detector level is disclosed. A photon-counting detector resolves the energy of each received X-ray, which is discernable from the output signal of the photon-counting detector. For example, the received X-ray can have any energy value, e.g., $E_1$, $E_2$, . . . , or $E_n$. Pre-loaded energy-correlated weights, denoted by $W(E_1)$, $W(E_2)$, . . . , $W(E_n)$, are used such that one of the weights is obtained for each corresponding X-ray photon having a given energy. For example, if an X-ray photon of energy $E_1$ is received, the weight $W(E_1)$ is obtained, e.g., from a look-up table. Note that a finite number of weights/energy levels can be used, or the weights can be a more general function of the energy. The optimum number of weights is determined by the energy resolution. For example, after reaching the optimum, adding more weights only costs more in the implementation, but does not gain anything in performance. The implementation can be a lookup table (with pre-calculated weights) or a function to be calculated in realtime using a DSP or an FPGA, for example.

Next, all of the obtained weights obtained in a predetermined scan or measurement period are summed to calculate an energy-weighted bin value.

In one embodiment, each weight can be proportional to a power of the corresponding energy E, where the power is dependent on the clinical application. For example, each weight $W(E_i)$ can be proportional to $1/E_i^3$.

Figure 3:
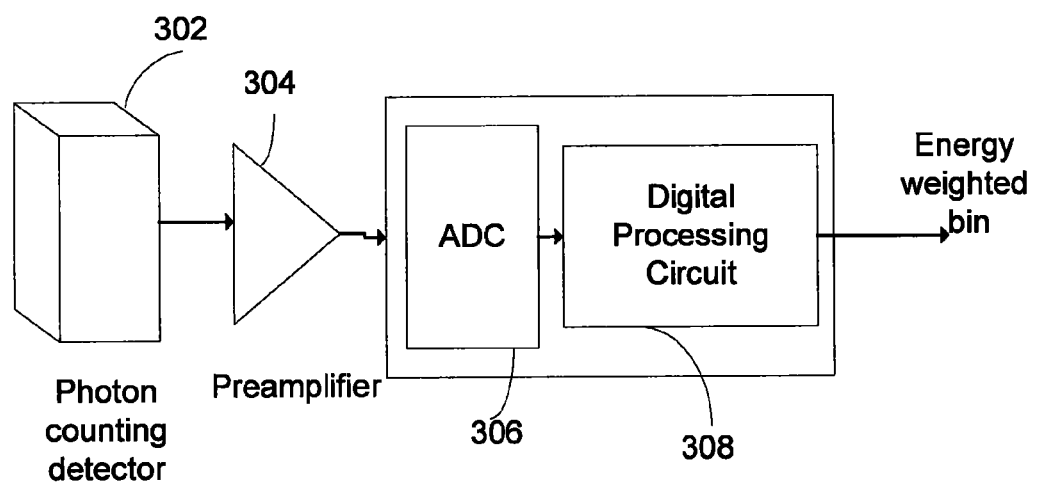
FIG. 3 is illustrates a device for performing energy-weighted binning.
Figure 4:
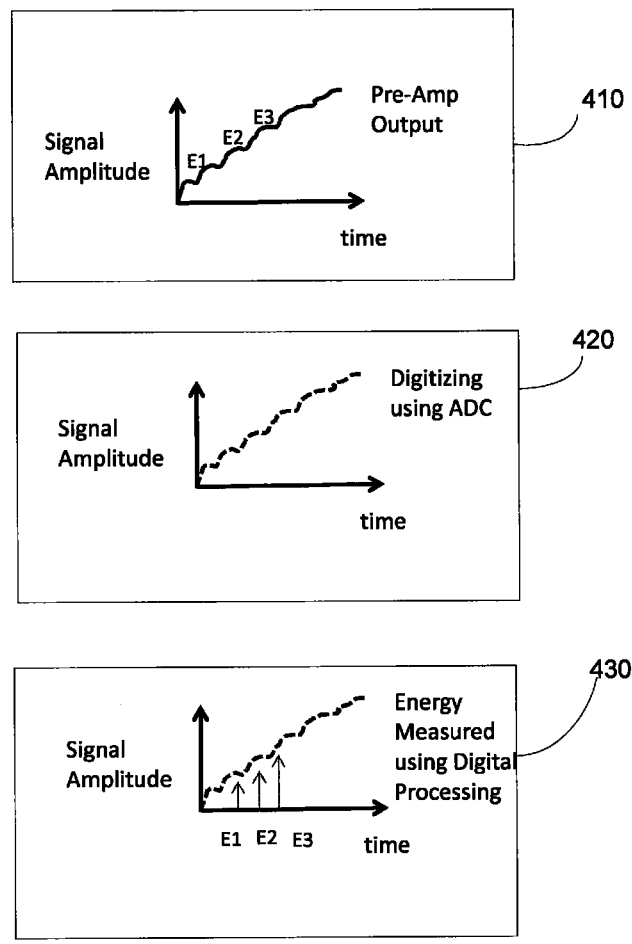
FIG. 4 illustrates signal outputs of elements of the device of FIG. 3.

FIG. 3 illustrated a practical device for implementing the detector-level energy-weighted disclosed herein. FIG. 3 uses a combination of a high-speed ADC (analog-to-digital converter) 306 and a digital processing circuit 308 to perform energy-weighted binning at the detector level. In FIG. 3, the output of photon-counting detector 302 is input into a preamplifier 304. The output of the preamplifier 304, which is shown in graph 410 in FIG. 4, is input into the ADC 306, which produces the digitized signal shown in graph 420 in FIG. 4. The digitized signal output from the ADC is input to the digital signal processing circuit 308.

As shown in graph 430 in FIG. 4, the digital processing circuit 308 analyzes the digitized signal output from the ADC in real time to detect a plurality of photons and their corresponding energy levels, and for each detected photon, e.g., having an energy E, obtains (e.g., using a look-up table) a weight $W_E$ corresponding to the energy level E of the photon. The digital processing circuit further sums of all the obtained weights $W_E$ during a measurement period to form the energy-weighted bin value.

Figure 2:
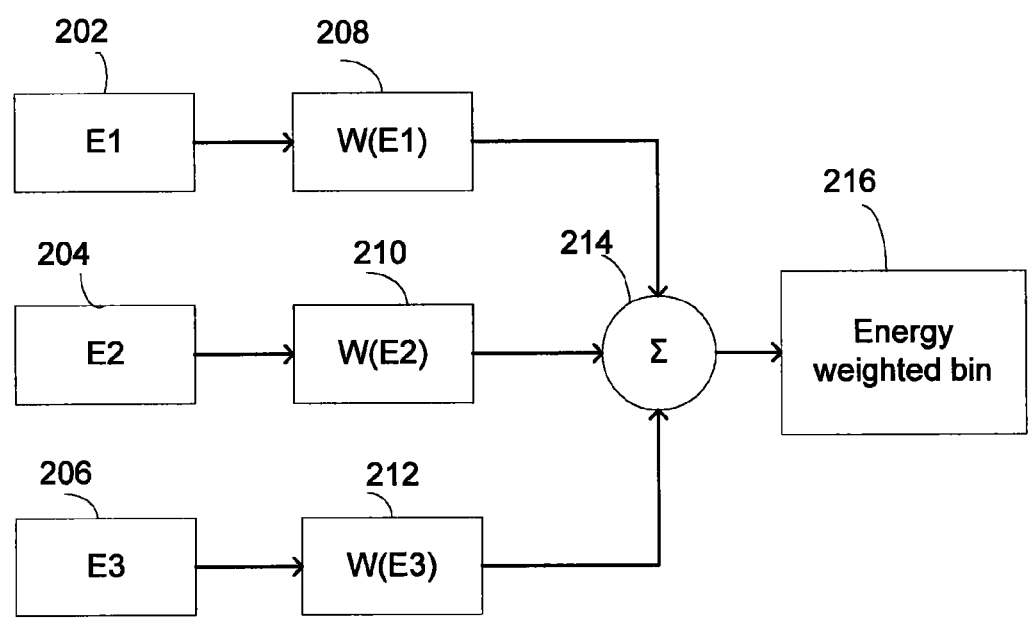
FIG. 2 illustrates energy-weighted binning.

Referring now to FIG. 2, FIG. 2 is a block diagram that shows how the energy-weighted bin value is obtained by the digital processing circuit according to one embodiment of the present disclosure. Elements 202, 204, and 206 represent a photon detected by the digital processing having a corresponding energy value E1, E2, and E3, respectively. Elements 208, 210, 212 represent weights W(E1), W(E2), W(E3) that are obtained corresponding to the energy values E1, E2, and E3, respectively. The weights are summed by the summer 214 to produce the energy-weighted bin value 216.

The disclosed embodiments have several advantages over conventional approaches, e.g., an improved contrast-to-noise ratio (CNR). Further, the disclosed detector-level energy weighting significantly reduces the processing time compared to image-domain energy weighting, while having the same CNR advantages. Further, in the present embodiments, the method of calculating the weights in the digital processing circuit can be easily modified to suit a particular application.

Figure 5:
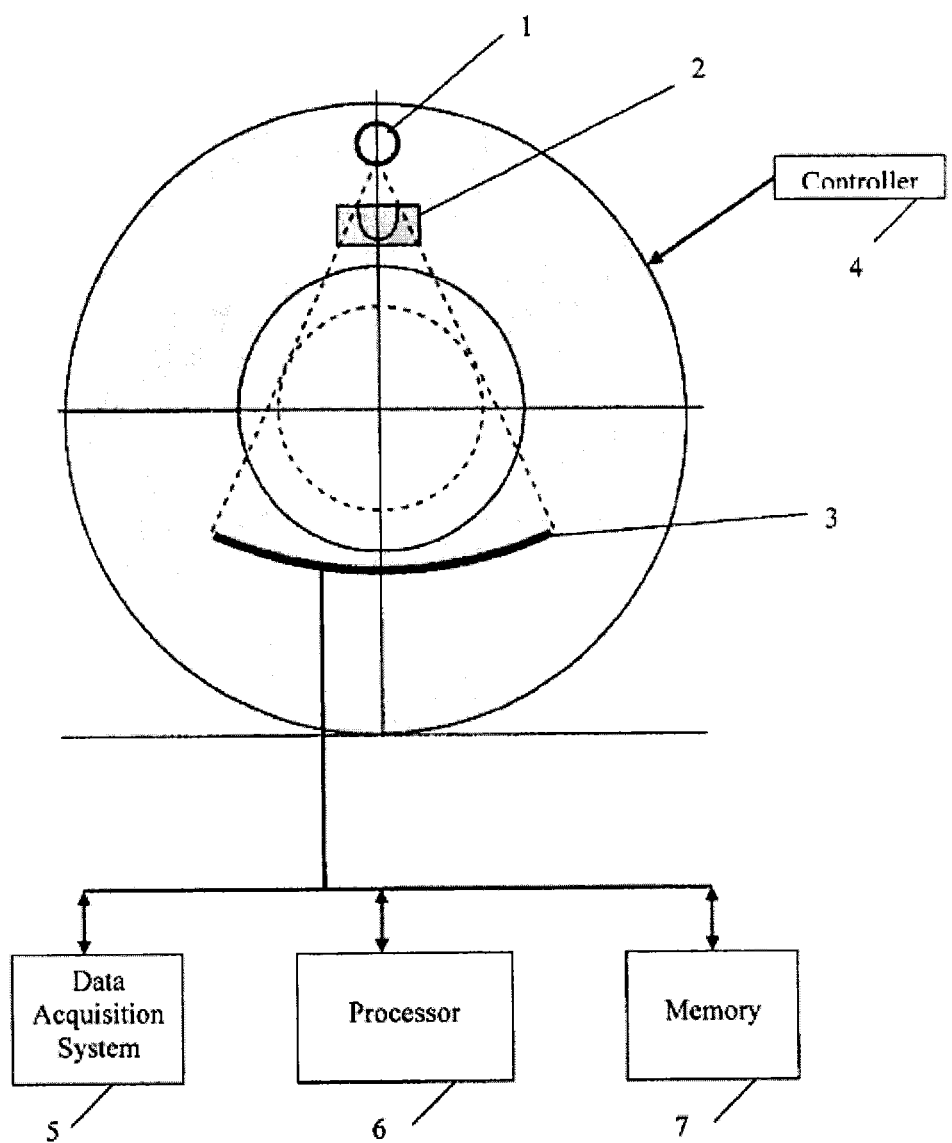
FIG. 5 illustrates a CT scanner system.

FIG. 5 illustrates the basic structure of a CT scanner apparatus that includes the detectors described herein. The CT apparatus of FIG. 5 includes an X-ray tube 1, filters and collimators 2, and detector 3. As shown in FIGS. 6A and 6B, the CT apparatus also includes sparse, fixed energy-discriminating detectors, creating a $4^{th}$-generation scanner. The CT apparatus will also include additional mechanical and electrical components such as a gantry motor and a controller 4 to control the rotation of the gantry, control the X-ray source, and control a patient bed. The CT apparatus also includes a data acquisition system 5 and a processor 6 to generate CT images based on the projection (view) data acquired by the data acquisition system. The processor 6 can be a CPU or other hardware processing circuit that can execute a computer program. The processor and data acquisition system make use of a memory 7, which is configured to store, e.g., projection data obtained from the detector and reconstructed images.

As one of ordinary skill in the art would recognize, the digital processing circuit 308 can include a CPU that can be implemented as discrete logic gates, as an Application Specific Integrated Circuit (ASIC), a Field Programmable Gate Array (FPGA), a DSP/GPU, or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the digital processing circuit 308 can execute a computer program including a set of computer-readable instructions that perform the functions described herein, the program being stored in any of the above-described non-transitory electronic memories and/or a hard disk drive, CD, DVD, FLASH drive or any other known storage media.

Further, the CPU in the processor 6 can be implemented as discrete logic gates, as an Application Specific Integrated Circuit (ASIC), a Field Programmable Gate Array (FPGA), a DSP/GPU, or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory.

Further, the CPU in the processor 6 can execute a computer program including a set of computer-readable instructions that perform various functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A computed tomography (CT) scanner system, comprising:
   an X-ray source;
   a plurality of photon-counting detectors, wherein each photon-counting detector is configured to receive X-ray photons from the X-ray source and to provide an output signal indicating a number of X-ray photons received; and
   a plurality of data acquisition devices, each data acquisition device including a digital processing circuit configured to
      obtain a digital signal corresponding to the output signal of a photon-counting detector;
      determine, from the obtained digital signal, a plurality of X-ray photons received by the photon-counting detector during a measurement period;
      determine a corresponding energy level of each of the plurality of X-ray photons;

determine, based on the corresponding energy level, a corresponding weight for each of the plurality of X-ray photons;

calculate a sum of the corresponding weights of the plurality of X-ray photons; and output the sum to processing circuitry; and the processing circuitry, which is configured to generate CT images based on each sum calculated and output by the plurality of data acquisition devices.

2. The CT scanner system of claim 1, wherein each data acquisition device further comprises:

an analog-to-digital converter circuit configured to generate the digital signal from the output signal of the photon-counting detector.

3. The CT scanner system of claim 2, wherein each data acquisition device further comprises:

a preamplifier configured to amplify the output signal of the photon-counting detector to generate an amplified signal, wherein the amplified signal is input to the analog-to-digital converter circuit.

4. The CT scanner system of claim 1, wherein the digital processing circuit is configured to determine the corresponding weight to be proportional to an inverse of the corresponding energy level cubed.

5. The CT scanner system of claim 1, wherein the digital processing circuit is configured to determine the corresponding weight by accessing a programmable look-up table.

6. The CT scanner system of claim 1, further comprising:

a memory configured to store the calculated sum as an energy-weighted bin value.

7. An apparatus, comprising:

a digital processing circuit configured to obtain a digital signal corresponding to an output signal of a photon-counting detector;

determine, from the obtained digital signal, a plurality of X-ray photons received by the photon-counting detector during a measurement period;

determine a corresponding energy level of each of the plurality of X-ray photons;

determine, based on the corresponding energy level, a corresponding weight for each of the plurality of X-ray photons;

calculate a sum of the corresponding weights of the plurality of X-ray photons; and output the sum to processing circuitry, which generates CT images based on received data including the calculated sum.

8. The apparatus of claim 7, further comprising:

an analog-to-digital converter circuit configured to generate the digital signal from the output signal of the photon-counting detector.

9. The apparatus of claim 7, further comprising:

a preamplifier configured to amplify the output signal of the photon-counting detector to generate an amplified signal, wherein the amplified signal is input to the analog-to-digital converter circuit.

10. The apparatus of claim 7, wherein the digital processing circuit is configured to determine the corresponding weight to be proportional to an inverse of the corresponding energy level cubed.

11. The apparatus of claim 7, wherein the digital processing circuit is configured to determine the corresponding weight by accessing a programmable look-up table.

12. The apparatus of claim 7, further comprising:

a memory configured to store the calculated sum as an energy-weighted bin value.

* * * * *